(12) United States Patent
Glauber et al.

(10) Patent No.: US 11,324,872 B2
(45) Date of Patent: May 10, 2022

(54) BI-DIRECTIONAL PERFUSION CANNULA

(71) Applicant: EDAY S.R.L., Milan (IT)

(72) Inventors: Mattia Glauber, Milan (IT); Angelo Passanante, Milan (IT)

(73) Assignee: EDAY S.R.L., Milan (IT)

( * ) Notice: Subject to any disclaimer, the term of this patent is extended or adjusted under 35 U.S.C. 154(b) by 292 days.

(21) Appl. No.: 16/633,866

(22) PCT Filed: Jul. 25, 2018

(86) PCT No.: PCT/IB2018/055555
§ 371 (c)(1),
(2) Date: Jan. 24, 2020

(87) PCT Pub. No.: WO2019/021215
PCT Pub. Date: Jan. 31, 2019

(65) Prior Publication Data
US 2020/0164134 A1    May 28, 2020
US 2021/0162111 A9    Jun. 3, 2021

(30) Foreign Application Priority Data
Jul. 26, 2017 (IT) .................. 102017000085305

(51) Int. Cl.
*A61M 1/36*    (2006.01)

(52) U.S. Cl.
CPC ........ *A61M 1/3659* (2014.02); *A61M 1/3613* (2014.02)

(58) Field of Classification Search
CPC .............. A61M 1/3613; A61M 1/3653; A61M 1/3655; A61M 1/3659; A61M 1/3661
See application file for complete search history.

(56) References Cited

U.S. PATENT DOCUMENTS 3,896,527 A    7/1975   Miller
4,114,618 A    9/1978   Vargas
(Continued)

FOREIGN PATENT DOCUMENTS

WO    WO-2019021215 A1    1/2019

OTHER PUBLICATIONS

International Search Report and Written Opinion dated Nov. 16, 2018 International Application No. PCT/IB2018/055555, EPO, Netherlands, 15 pages.

*Primary Examiner* — Philip R Wiest
(74) *Attorney, Agent, or Firm* — Sterne, Kessler, Goldstein & Fox P.L.L.C.

(57) ABSTRACT

A bi-directional perfusion cannula comprising a flexible elongated tube 1 for insertion into an artery having a first aperture 3 at a distal end and a second aperture 4 formed rearward of the first aperture, the elongated tube can be bent in correspondence of the second aperture to orient it in a direction opposite to the insertion direction. The cannula is provided with a tape 5 having a first end portion shaped as a ring, fixed on an outer surface of the elongated tube, and a second end portion opposite to the first end portion either coupled to or being integral with a belt 7 defining a strap 11 with holes 12 and at least a prong 13 integral with the strap and configured to engage a respective hole, wherein the belt is configured to be tightened around an outer surface of the artery.

6 Claims, 13 Drawing Sheets

(56) References Cited

U.S. PATENT DOCUMENTS

| | | | |
|---|---|---|---|
| 5,330,498 A * | 7/1994 | Hill | A61B 17/12022 |
| | | | 604/907 |
| 5,599,329 A | 2/1997 | Gabbay | |
| 2012/0259273 A1 * | 10/2012 | Moshinsky | A61M 1/3659 |
| | | | 604/28 |

* cited by examiner

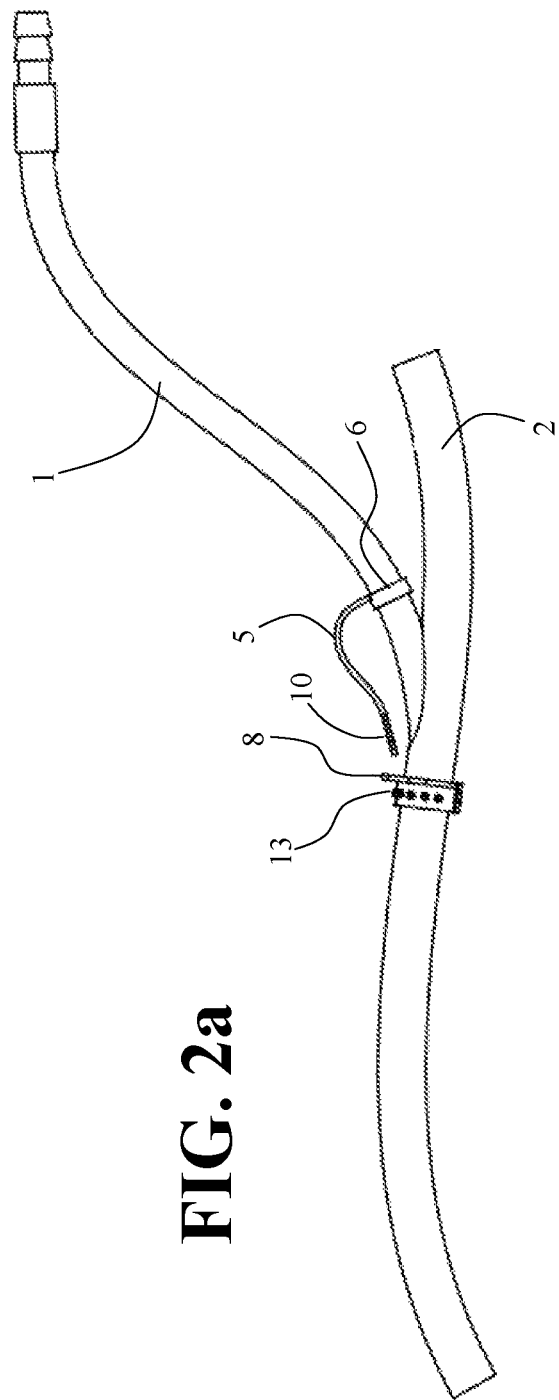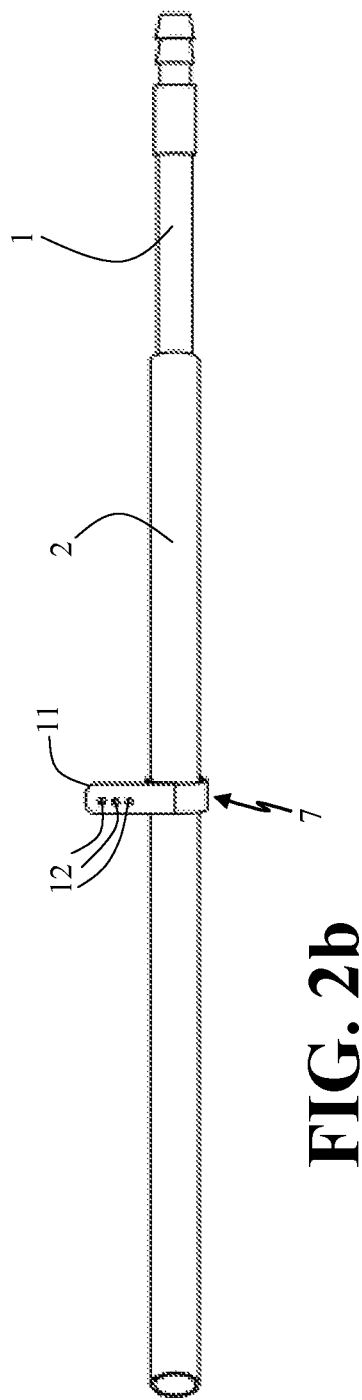
FIG. 2a
FIG. 2b

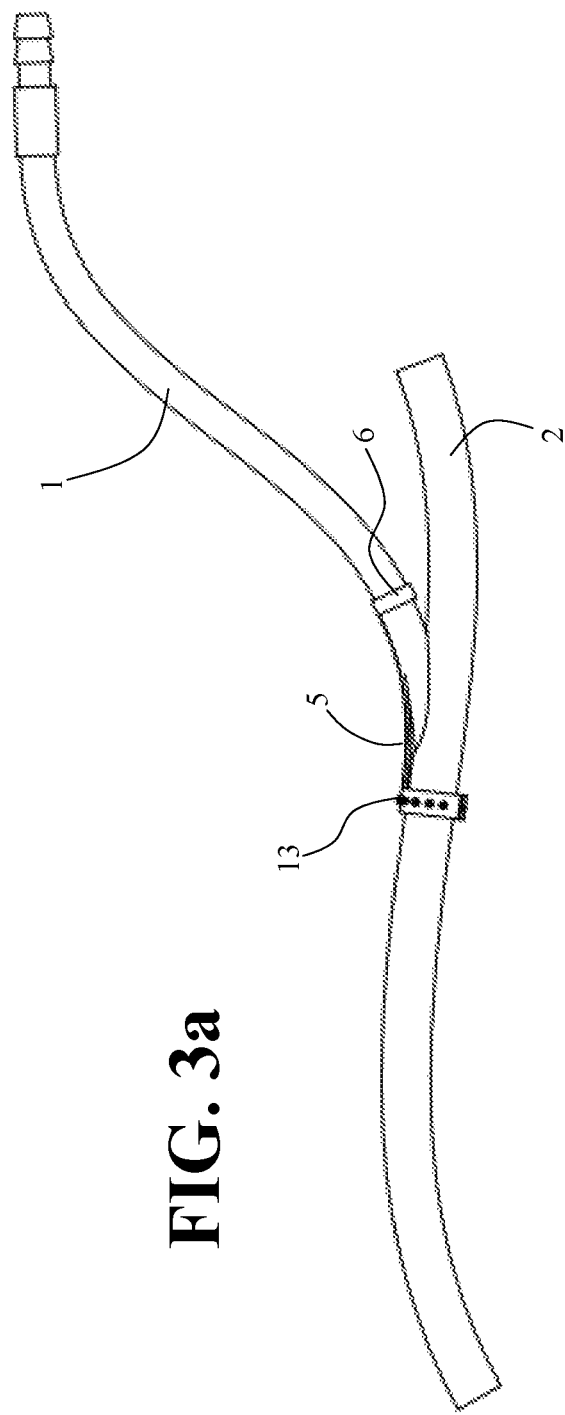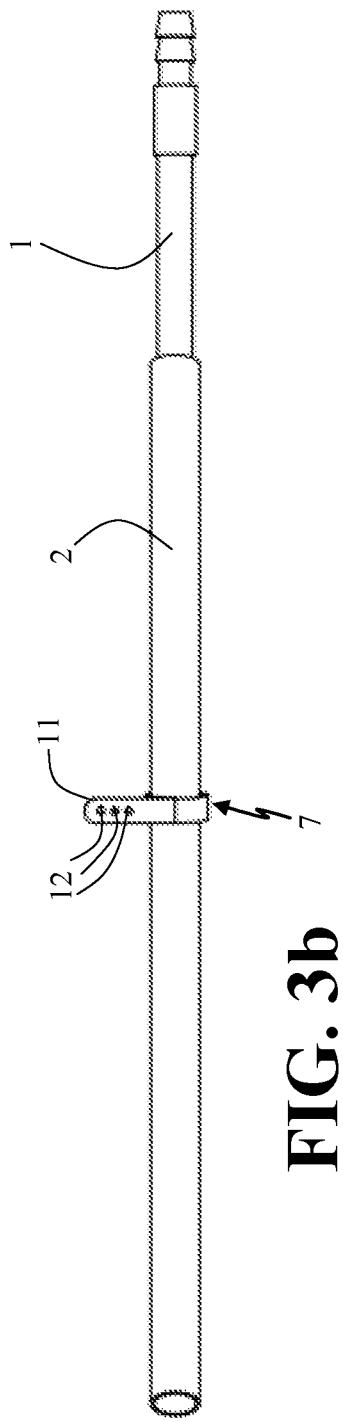
FIG. 3a
FIG. 3b

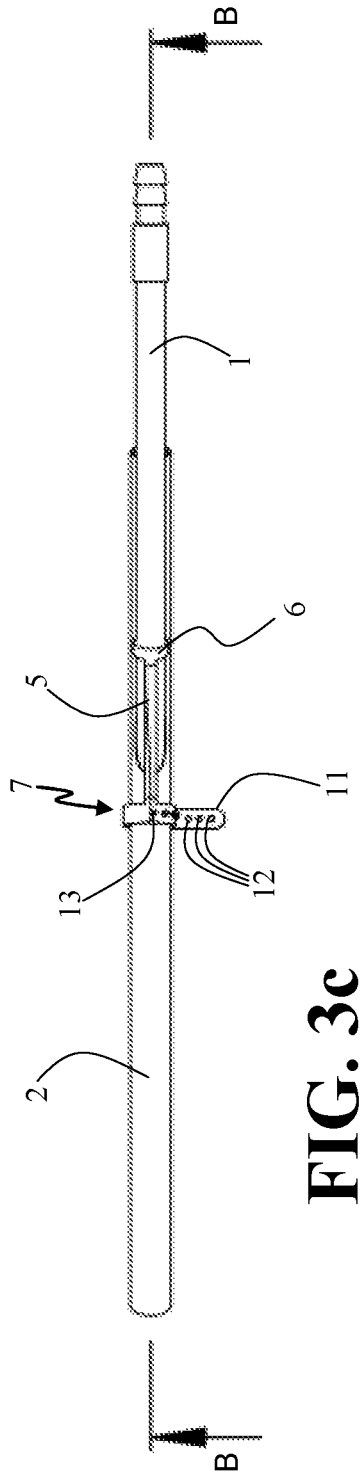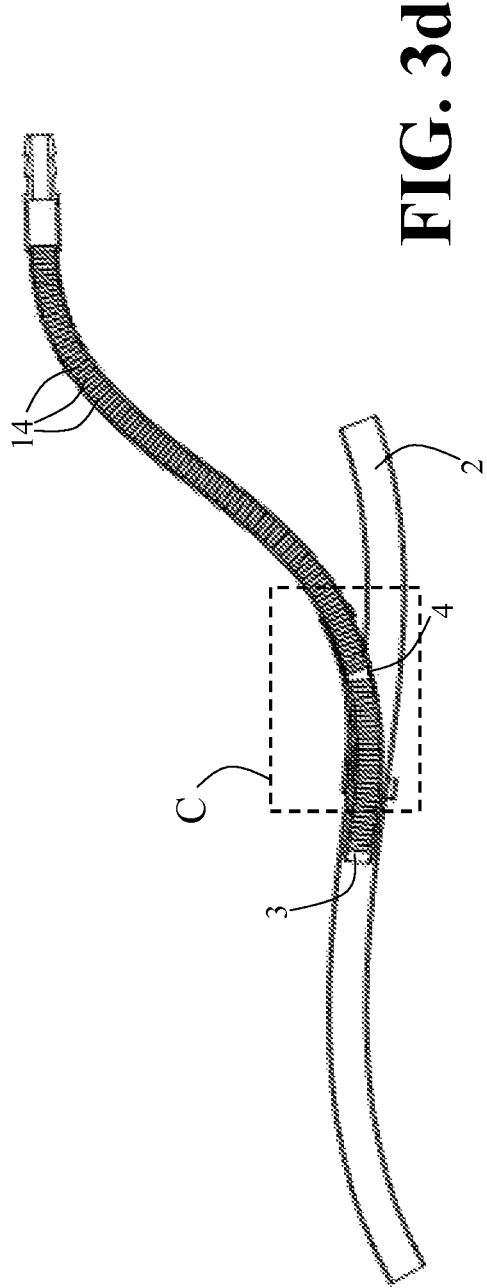

BI-DIRECTIONAL PERFUSION CANNULA

TECHNICAL FIELD

This disclosure relates to perfusion cannulas and more particularly to a bi-directional perfusion cannula configured to be anchored to an artery in which it is inserted.

BACKGROUND

Some cardiac surgery procedures require peripheral artery cannulation for cardiopulmonary bypass. Also, some disease states require mechanical cardiopulmonary support via peripheral artery cannulation.

To provide increased blood flow to the distal extremity, the cannula may be provided with bi-directional fluid flow capability. Various bi-directional perfusion cannulas have been proposed. One approach has been to use a perfusion cannula with a diameter significantly smaller than the blood vessel lumen diameter in order to permit some blood to flow back over the perfusion cannula, but such systems must be carefully designed and positioned in order to assure appropriate blood flow in the retrograde and forward direction.

Another approach, disclosed in US2012/0259273 and illustrated in FIG. 1, has been to realize a bi-directional perfusion cannula comprising an elongated tube for insertion into an artery, the elongated tube comprising: a first aperture at a distal end of the tube which is forward during insertion, the first aperture being configured so that blood can flow into the artery in the direction of insertion; an elbow 28 formed in the elongate tube; and a second aperture 18, the second aperture being formed in or slightly rearward of the elbow and configured for supplying blood into the artery in a second direction which is generally opposite to the insertion direction. The elongated tube has a protuberance 20 at least partially formed on the elbow, the protuberance being configured to facilitate positioning of the cannula in the artery, so as the protuberance and the elbow form a transition zone which splints open the artery. A metal wire is spirally wound in the body of the cannula to make more robust the cannula. In order to make easier to bend the cannula in correspondence of the elbow, the metal wire is wounded with an augmented step in correspondence of the second aperture.

It is well known that the prior cannula illustrated in FIG. 1 can be used in sedated patients. Indeed, even if the elbow obstacles the cannula from exiting from the artery in which it is inserted, movements of the awake patient may cause the elbow of the cannula slip out of the artery leading to patient's death.

Moreover it has been noticed that, even in completely sedated patients, the cannula tends to slip out of the artery in which it is inserted and should be repositioned repeatedly, or fixed to the patient's skin. Without being bound to a theory, this drawback could be due to blood pressure of patients, that pushes the cannula out of the artery.

In general, the fact that the patient must be sedated as far as the cannula is inserted in an artery, may raise typical problems due to prolonged immobility of the patient, which are considered practically unavoidable in the art and are accepted as a tradeoff.

SUMMARY

Even if arterial cannulas are considered safely usable only (or preferably) on completely sedated patients, the applicant has conducted extensive studies aimed to realize a cannula usable also with awake patients, in order to prevent problems due to prolonged immobility and to make the patients live while staying conscious.

From these studies, it has been noticed that arteries in which a cannula is typically inserted are relatively robust. This observation made the applicant conscious that outer fixing elements may be tied outside the arteries instead of inside the arteries, like the elbow of the prior cannula, in order to bind the cannula firmly without damaging the outer tissue of the respective artery even if the patient is moving.

According to this disclosure, a bi-directional perfusion cannula comprises a flexible elongated tube for insertion into an artery having a first aperture at a distal end of the elongated tube, oriented forward during insertion into an artery, configured so that blood can flow into the artery in a direction of insertion, a second aperture formed rearward of the first aperture and configured to supply blood into the artery in a second direction, wherein the elongated tube can be bent in correspondence of the second aperture in order to orient it in a direction opposite to the insertion direction. The outstanding results mentioned above have been obtained by providing the bi-directional perfusion cannula with a tape having a first end portion shaped as a ring, fixed on an outer surface of the elongated tube, and a second end portion opposite to the first end portion either configured to be coupled to or being integral with a belt defining a strap with holes and at least a prong integral with the strap and configured to engage a respective hole, wherein the belt is made of a bio-compatible material and is configured to be tightened around an outer surface of the artery at a distance from a point of insertion of said elongated tube in the artery, so as to tighten the artery together with the elongated tube.

The claims as filed are integral part of this specification and are herein incorporated by reference.

Figures from 2a to 2h depict different views of a bi-directional perfusion cannula according to an embodiment of this disclosure, having a tape with an end portion fixed to the cannula and the opposite end portion connectable to a belt having a strap with holes and at least a prong.

Figure from 3a to 3h depict different views of a bi-directional perfusion cannula according to an embodiment of this disclosure, having a tape with an end portion fixed to the cannula and the opposite end portion integral with a belt having a strap with holes and at least a prong.

DETAILED DESCRIPTION

Figure 2E:
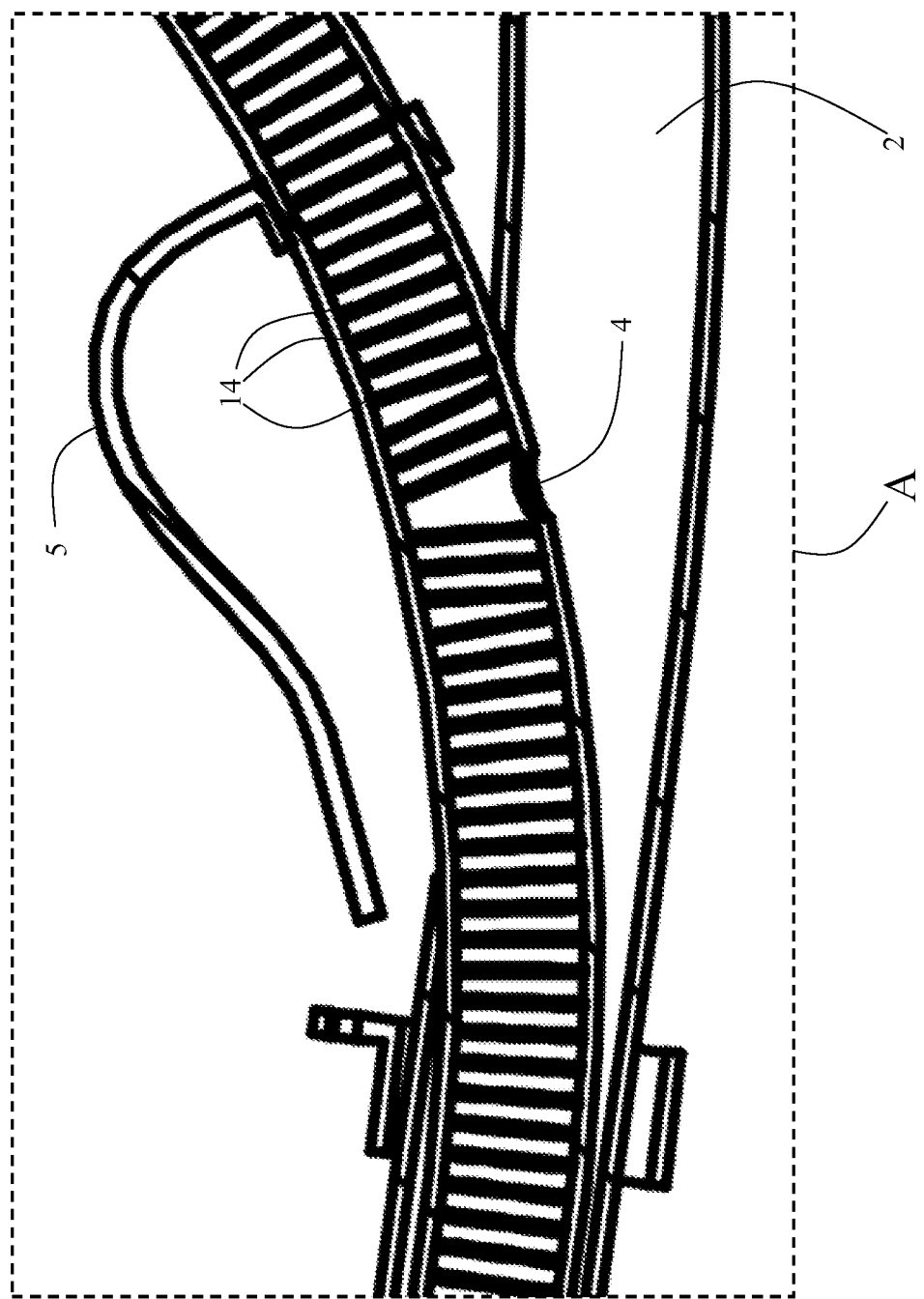
Figure 2F:
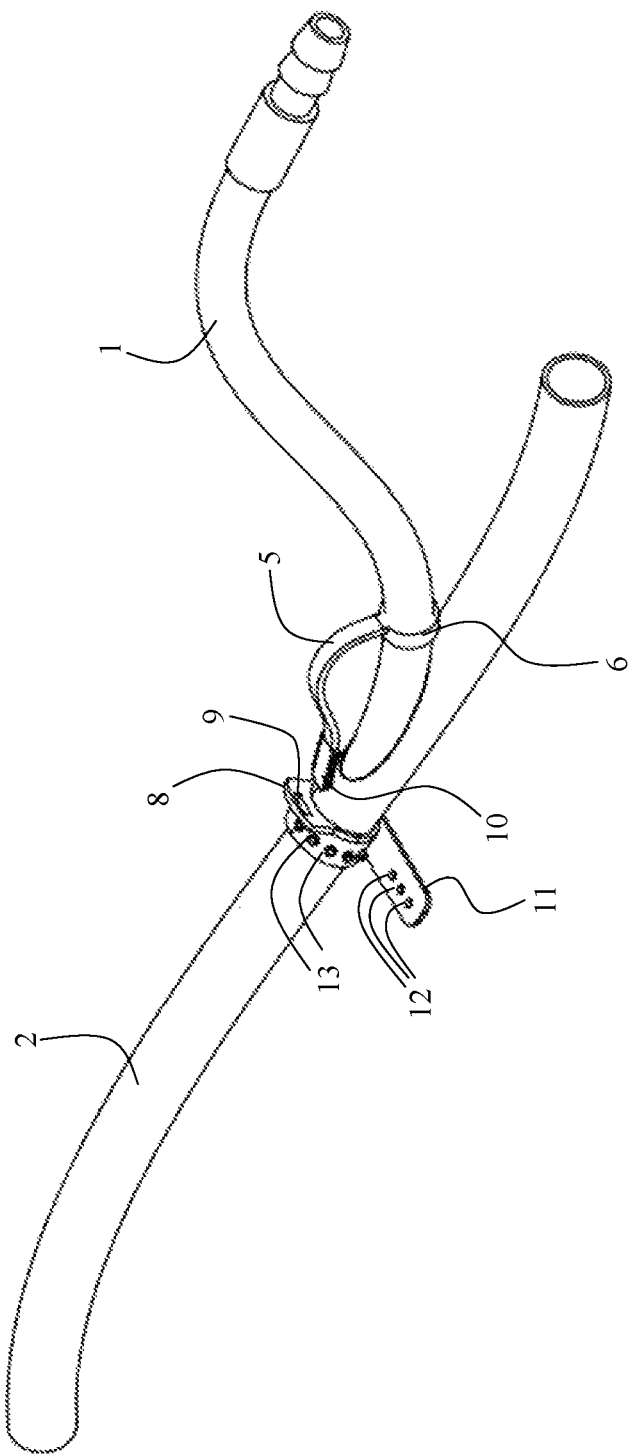
Figure 2G:
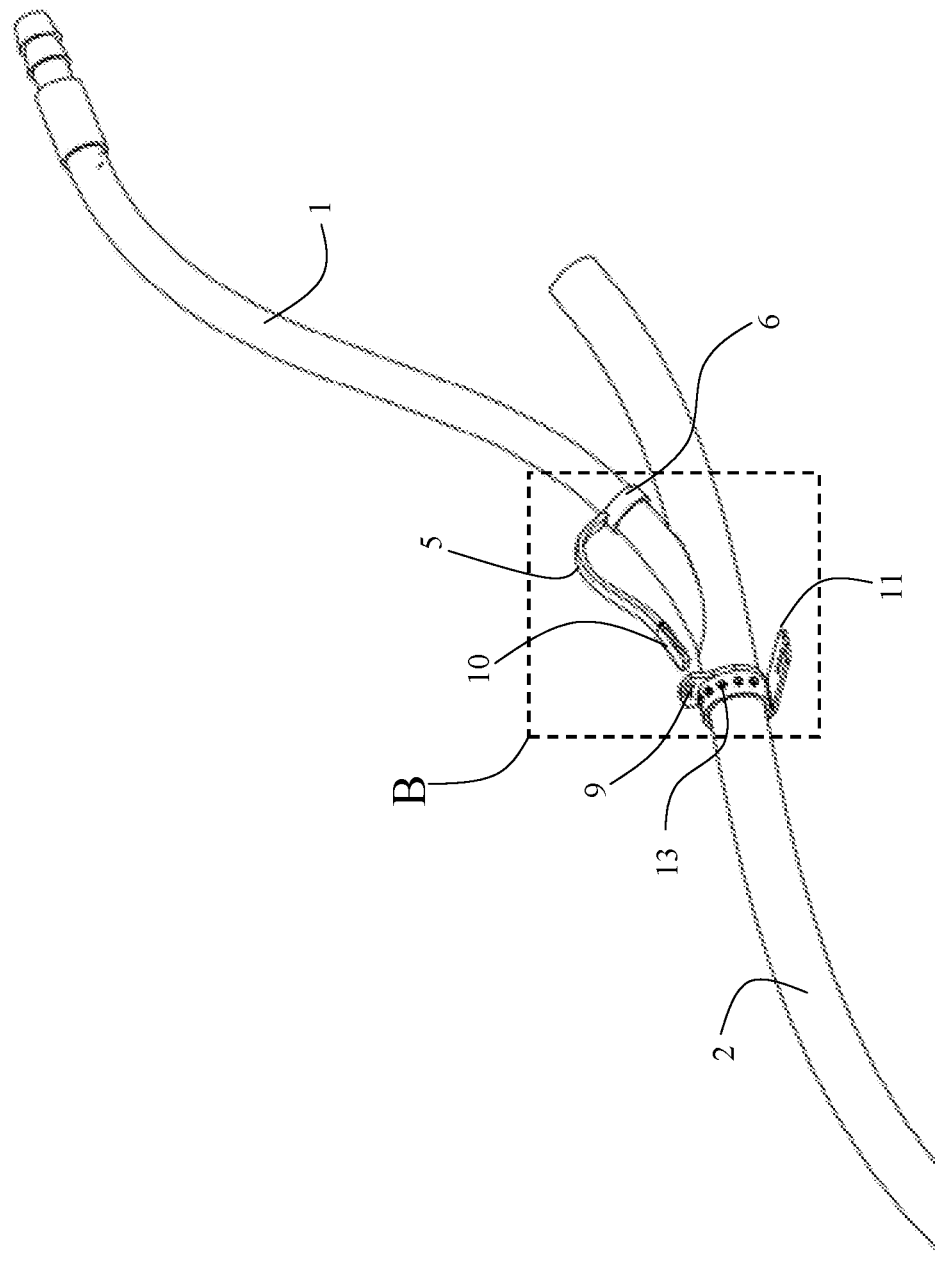
Figure 2H:
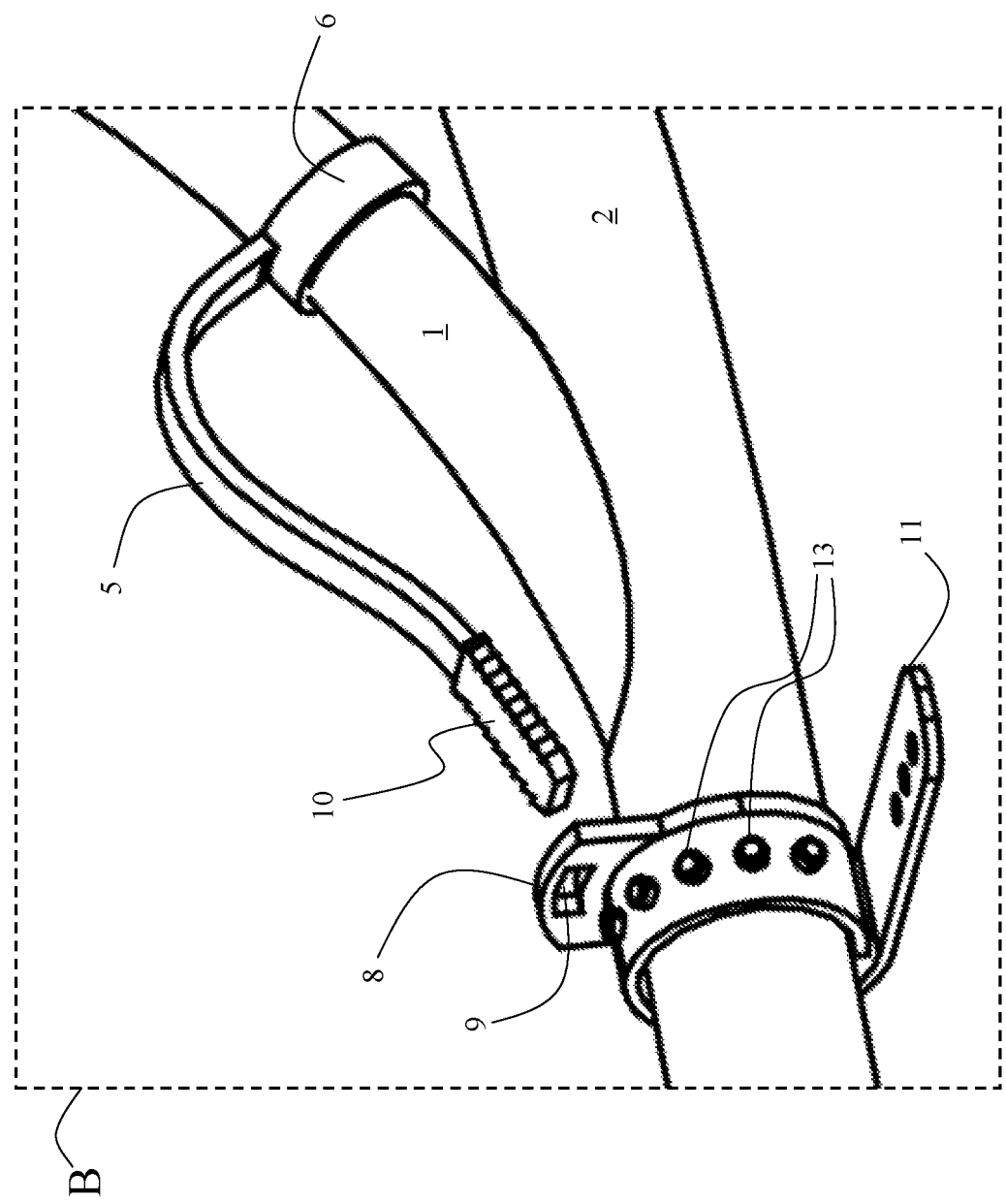
Figure 3E:
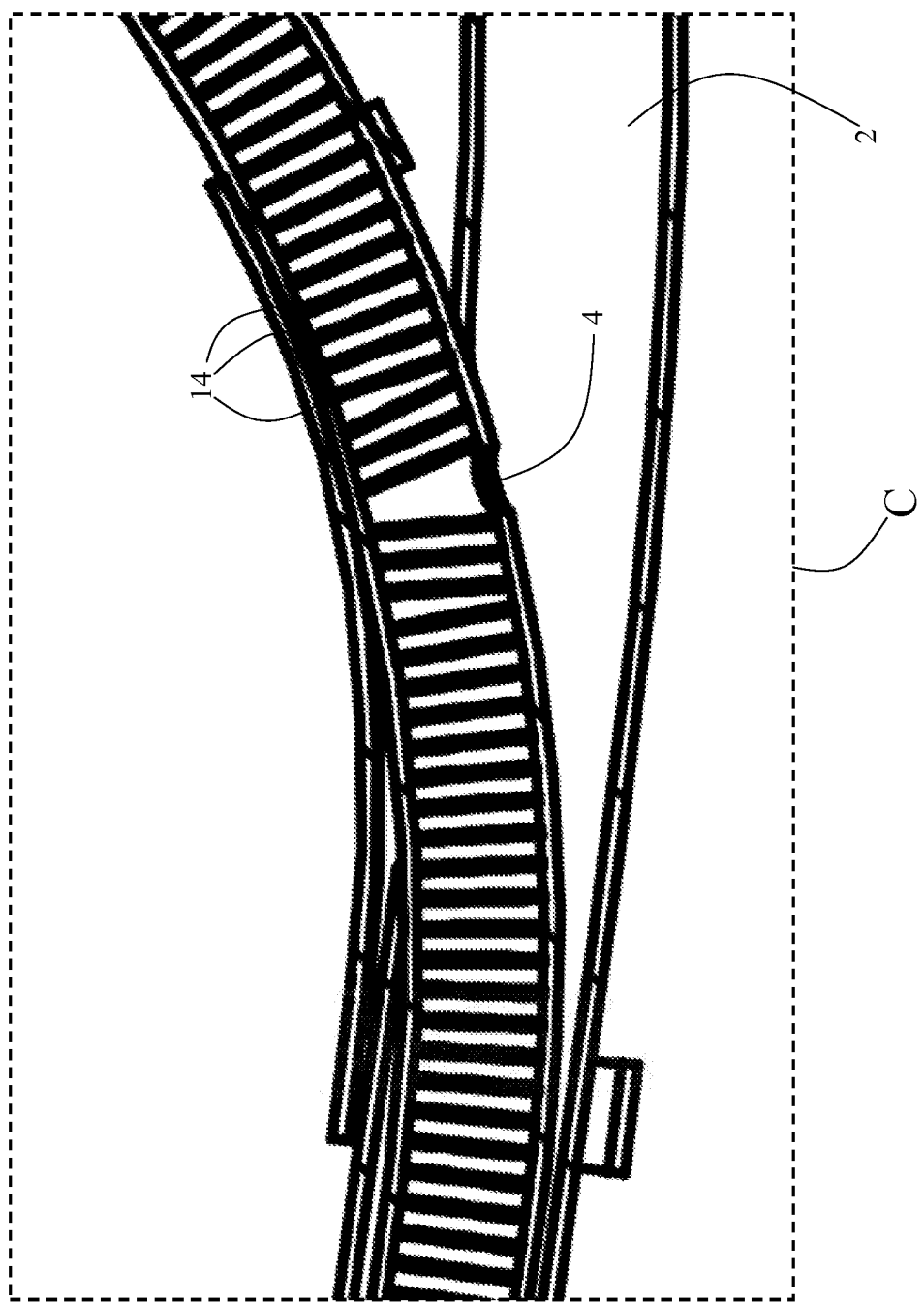
Figure 3F:
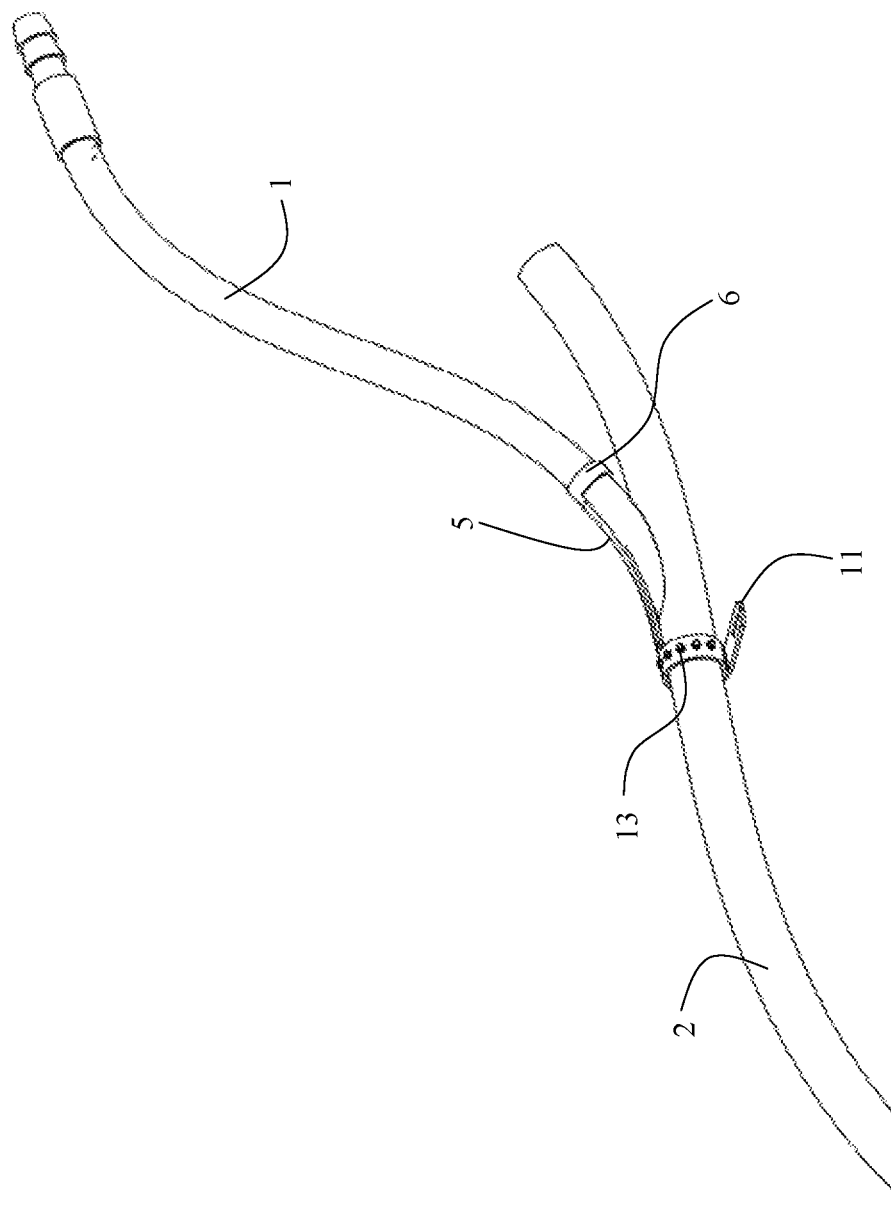
Figure 3G:
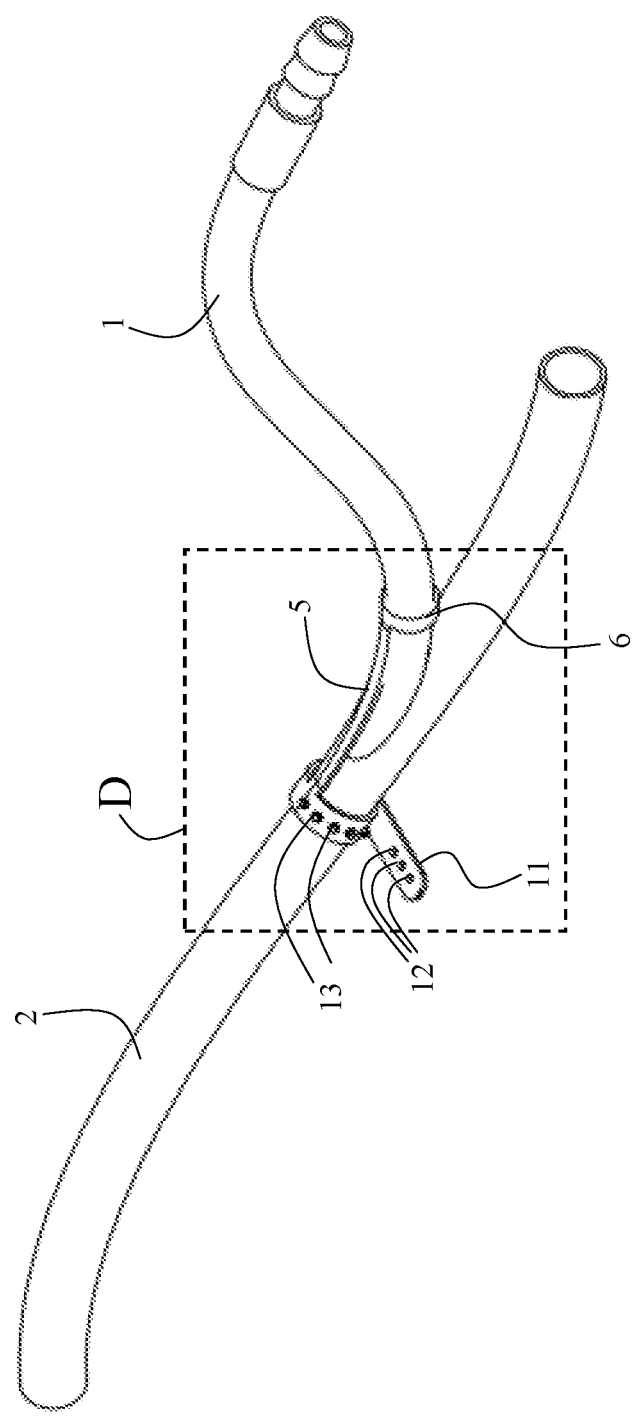
Figure 3H:
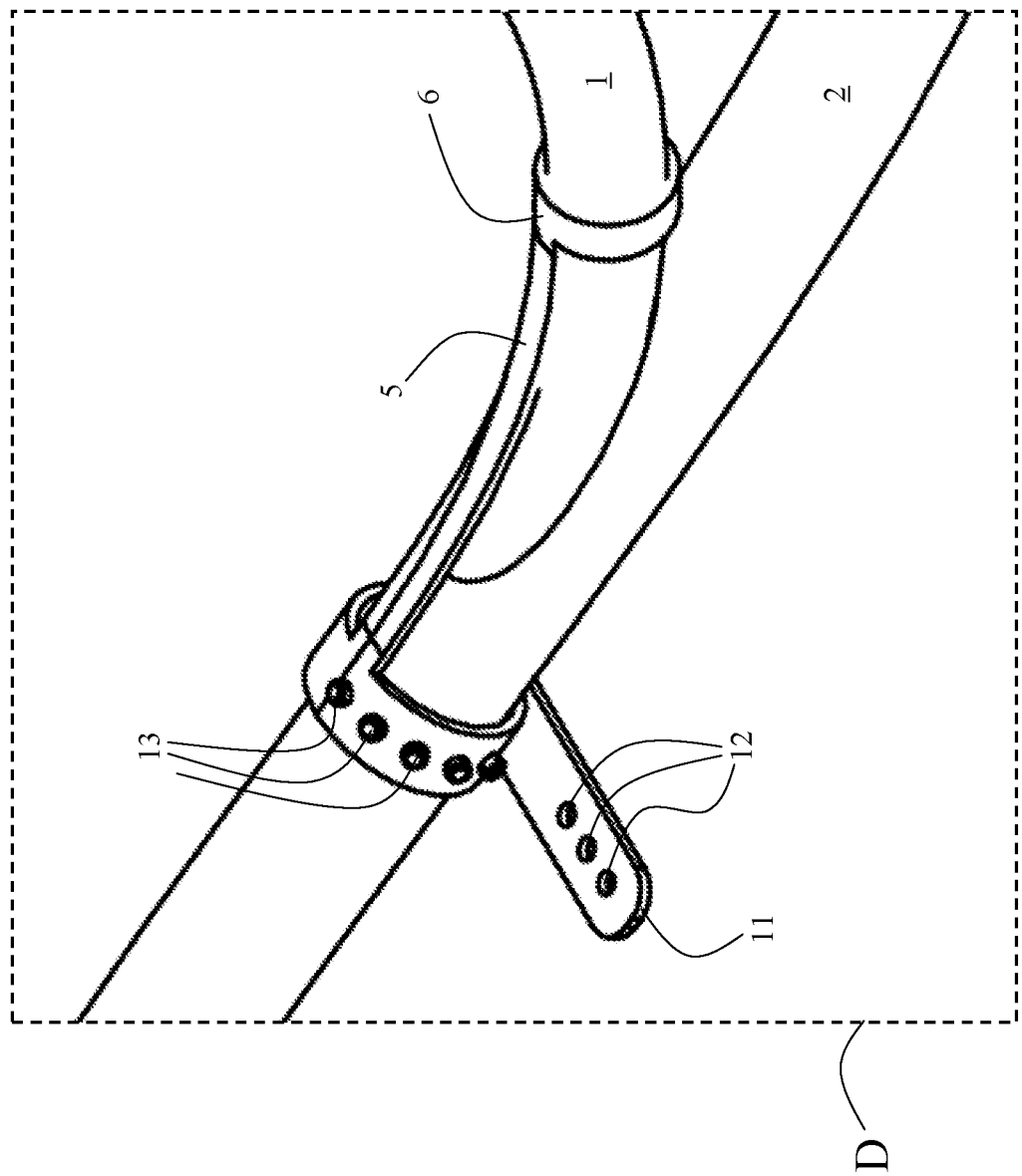

Various views of two different exemplary embodiments of a bi-directional perfusion cannula of this disclosure are depicted in figures from 2a to 2h and from 3a to 3h, respectively. The perfusion cannula comprises a flexible elongated tube 1 adapted to be inserted into an artery 2. As the prior cannula depicted in FIG. 1 the elongated tube has a first aperture at a distal end, to inject blood in the direction of insertion of the tube 1 into the artery 2, and a second aperture 4, that is more clearly shown in the sectional views of detail of FIGS. 2e and 3e. The flexible tube 1 is adapted to be bent so as the second aperture 4 can be oriented to inject blood in a direction opposite to the insertion direction of the first aperture 3 for letting blood to flow also in the retrograde direction. When in use, a distal portion of the tube 1, comprised between the first aperture and the second aperture 4, lays longitudinally in the artery 2.

In order to anchor firmly the tube 1 to the artery 2, the cannula of this disclosure comprises a tape 5, made of bio-compatible material, connected from a first end to a ring 6 fixed to the tube 1, and a belt 7 tightened around the artery 2.

According to the embodiment of figures from 2a to 2h, the tape 5 may be connected to the belt 7 after the tube 1 has been inserted into the artery 2. This is made possible because the belt 7 has a head 8 with a pawl 9, and the free end of the tape 5 has teeth 10 so as to engage with the pawl 9 to form a ratchet as a cable tie. With this solution, it is possible to adjust the length of the tape 5 suspended between the ring 6 and the head 8 so as to tighten it and prevent the tube 1 from slipping out of the artery 2.

As an alternative, illustrated in figures from 3a to 3h, the tape 5 may be integral with the belt 7. The cannula according to this latter embodiment is simpler from a constructive point of view and easier to use than the former one, but requires an accurate positioning of the belt 7 for tightening the tape 5.

Figure 2C:
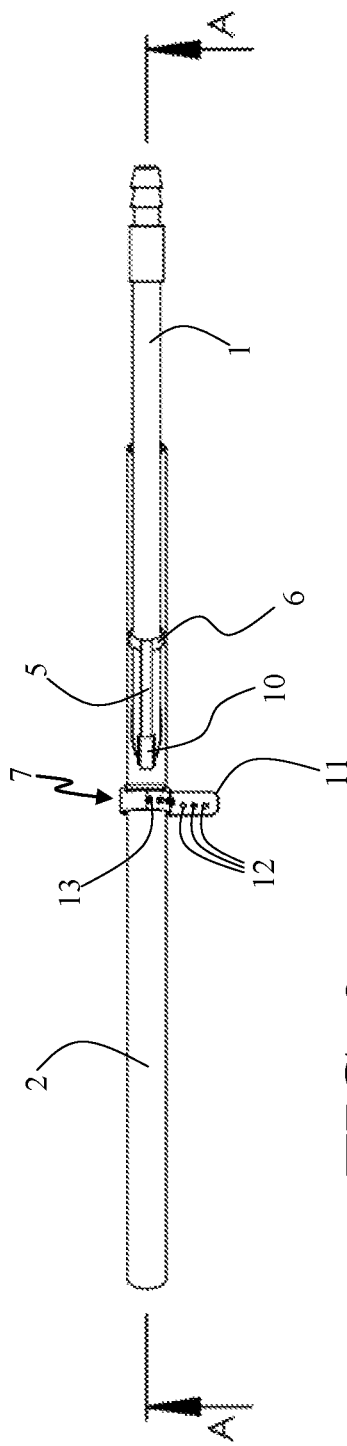
Figure 2D:
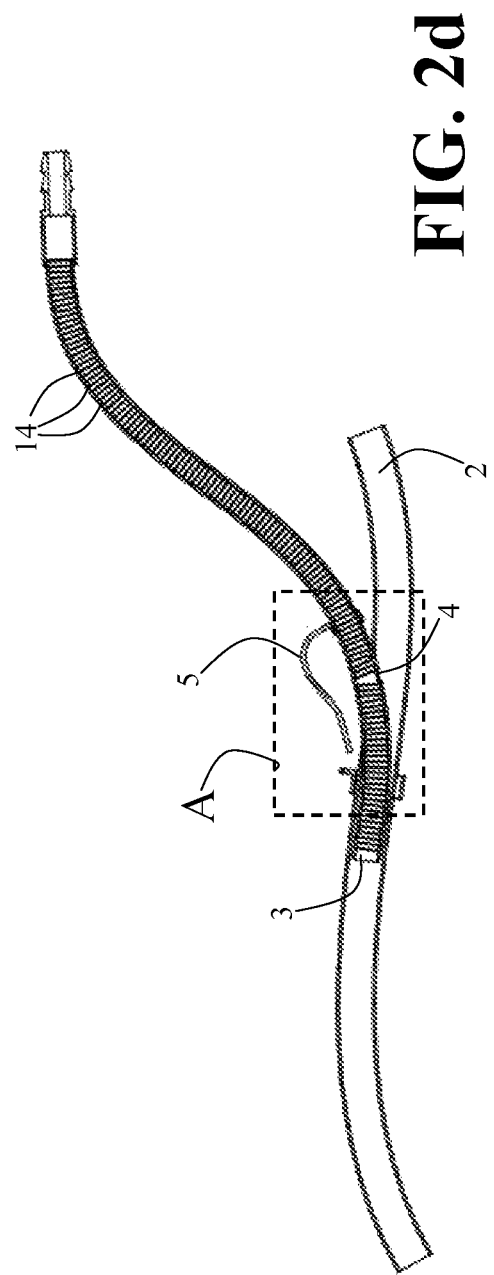

For both embodiments, the tube 1 is anchored to the artery 2 by tightening the tape 5 between the ring 6 and the belt 7, and by fastening the belt 7 so as to tighten the artery 2 together with the tube 1, as shown in FIGS. 2d and 3d. In practice, the tape 5 is long enough to allow to tighten the belt 7 at a distance from a point of insertion of the elongated tube 1 in the artery 2, so as to tighten the artery 2 together with the distal portion of the elongated tube 1 that lays longitudinally in the artery 2. In this way, blood is perfused in both directions by the forward aperture 3 and by the aperture 4 directed rearward, whilst there is no risk that the tube 1 slips out of the artery 2 even if the patient is awake and is moving.

In order to fasten tight the belt 7, the belt 7 has a strap 11 with spaced holes 12 and at least a prong 13, integral with the strap, configured to engage a respective hole 12. In the shown embodiment a plurality of prongs 13 are depicted, though a single prong 13 may be sufficient for holding fastened the belt 7. It is considered more convenient to have prongs 13 integral with the strap instead of having a buckle (not shown) as in common belts, because a buckle would concentrate the pressure exerted by the belt 7 in certain parts of the side surface of the artery 2, instead of letting it be distributed uniformly.

Conveniently, the area of the second aperture 4 may be up to 50% of the area of the forward aperture 3. Experiments carried out using working prototypes have shown that good performances in terms of forward and retrograde blood perfusion may be attained making the ratio between the sectional area of the second aperture 4 and of the first aperture 3 range between 25% and 30%.

Figure 1:
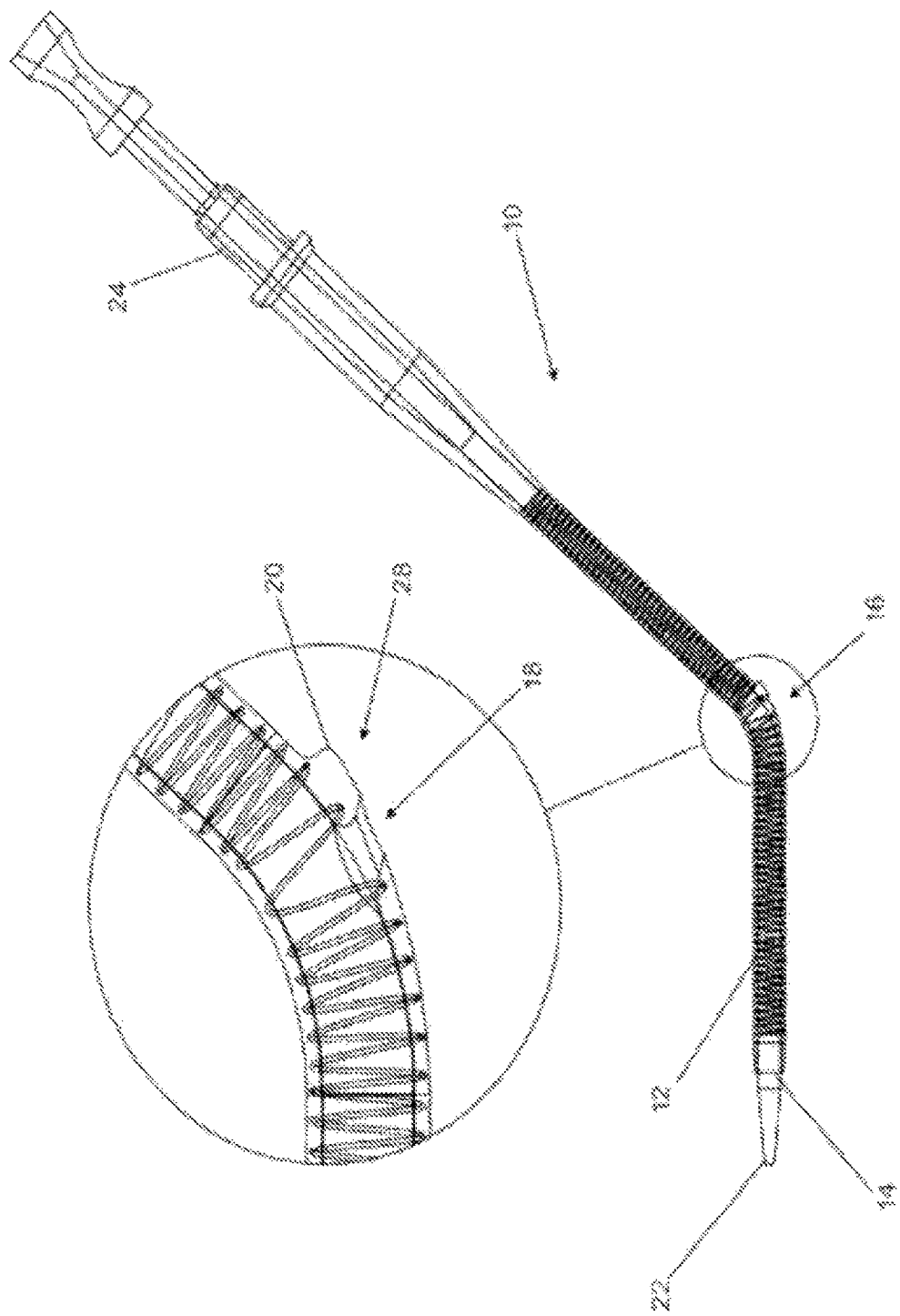
FIG. 1 depicts a side view of a prior bi-directional perfusion cannula with an introducer received therein.

As in the prior cannula of FIG. 1, the cannulas of this disclosure preferably incorporate a metal wire 14 spirally wound in the body of the tube 1 to make it more robust. In order to make easier to bend the tube 1 in correspondence of the second aperture 4, the metal wire 14 is wounded with an augmented step in correspondence of the second aperture 4. According to an alternative, not depicted in the enclosed drawings, instead of having a wound metal wire, the elongated tube may be reinforced with an outer bio-compatible metal cover, shaped so as to allow bending of the cannula in correspondence of the second aperture 4 whilst preventing kink of the tube. Metal covers of this type, presently used for example in the cannula marketed by Medtronic™ under the commercial name Bio-Medicus™ NextGen Cannulae, are designed to deform plastically for allowing to bend the cannula in a controlled fashion.

All parts of the bi-directional perfusion cannula of this disclosure are made of a bio-compatible material, in order to be adapted to be used within human body.

The invention claimed is:

1. A bi-directional perfusion cannula, comprising a flexible elongated tube for insertion into an artery configured to lay longitudinally in the artery, having:
   a first aperture oriented forward during insertion into an artery at a first end of a distal portion of the elongated tube, said distal portion of the elongated tube being configured to lay longitudinally in the artery, said first aperture being configured so that blood can flow into the artery in a direction of insertion,
   a second aperture formed rearward of the first aperture at a second end of said distal portion of the elongated tube, and configured to supply blood into the artery in a second direction,
   said elongated tube being configured to be bent in correspondence of said second aperture in order to orient said second aperture in said second direction opposite to the insertion direction,
   characterized in that the bi-directional perfusion cannula comprises:
   a tape having a first end portion shaped as a ring, fixed on an outer surface of the elongated tube, and a second end portion opposite to the first end portion, said second end portion being either configured to be coupled to or being integral with a belt defining a strap with holes and at least a prong integral with said strap and configured to engage a respective one of said holes, said belt being made of a bio-compatible material and being configured to be tightened around an outer surface of the artery;
      wherein said tape is configured to allow to tighten said belt at a distance from a point of insertion of said elongated tube in the artery, so as to tighten the artery together with the distal portion of the elongated tube when said distal portion of the elongated tube lays longitudinally in the artery.

2. The bi-directional perfusion cannula of claim 1, wherein
   said belt being integral with a head with a pawl, configured to engage with teeth of said second end portion;
   said second end portion is configured to be coupled with said belt and has teeth configured to engage with the pawl of said head to form a ratchet as a cable tie.

3. The bi-directional perfusion cannula of claim 1, comprising a metal wire incorporated into the flexible elongated tube as a spiral, wherein said spiral has an augmented step in correspondence of said second aperture.

4. The bi-directional perfusion cannula of claim 1, comprising a plurality of prongs integral with said strap.

5. The bi-directional perfusion cannula of claim 1, wherein said second aperture has a sectional area up 50% of a corresponding sectional area of said first aperture.

6. The bi-directional perfusion cannula of claim 5, wherein said second aperture has a sectional area ranging between 25% and 30% of a corresponding sectional area of said first aperture.

* * * * *